United States Patent
Prachar et al.

(10) Patent No.: US 10,939,668 B1
(45) Date of Patent: Mar. 9, 2021

(54) SYSTEMS AND METHODS FOR A MOSQUITO FITNESS TESTER

(71) Applicant: Verily Life Sciences LLC, Mountain View, CA (US)

(72) Inventors: Timothy Prachar, Menlo Park, CA (US); Robert Sobecki, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 517 days.

(21) Appl. No.: 15/268,678

(22) Filed: Sep. 19, 2016

(51) Int. Cl.
*A01K 29/00* (2006.01)
*A01K 1/03* (2006.01)
*A01K 67/033* (2006.01)
*H04R 1/02* (2006.01)
*G01S 15/88* (2006.01)

(52) U.S. Cl.
CPC ............ *A01K 29/005* (2013.01); *A01K 1/031* (2013.01); *A01K 67/033* (2013.01); *G01S 15/88* (2013.01); *H04R 1/028* (2013.01)

(58) Field of Classification Search
CPC ..... A01K 29/005; A01K 1/031; A01K 67/033
USPC ........ 119/236, 421, 6.5; 43/132.1, 133, 138, 43/107, 140, 142
See application file for complete search history.

(56) References Cited

U.S. PATENT DOCUMENTS

| | | | | |
|---|---|---|---|---|
| 1,135,710 A * | 4/1915 | Murphy | ................. | A01M 1/02 43/111 |
| 1,632,276 A * | 6/1927 | La Torriente | ........... | A01M 1/02 43/111 |
| 2,861,132 A * | 11/1958 | Kahn | .................... | A01M 1/023 367/139 |
| 2,928,204 A * | 3/1960 | Kahn | ..................... | A01M 1/02 43/107 |
| 2,992,343 A * | 7/1961 | Meijer | ................... | G11B 17/00 310/76 |
| 4,160,824 A * | 7/1979 | Inazuka | ............... | A01N 25/006 424/84 |
| 4,438,585 A * | 3/1984 | Slatton | .................... | A01M 1/02 43/113 |
| 4,968,974 A * | 11/1990 | Sakano | .................. | A01K 1/031 119/421 |
| 5,594,654 A * | 1/1997 | Shuman | ............... | A01K 67/033 700/213 |
| 5,816,256 A * | 10/1998 | Kissinger | ............... | A01K 1/031 128/897 |
| 6,707,384 B1 * | 3/2004 | Shuman | ............. | G01N 15/1456 250/336.1 |

(Continued)

OTHER PUBLICATIONS

Mahmoud, M. F. et al.; "Effect of gamma radiation on the male sterility and other quality parameters of peach fruit fly"; Hort. Sci.(Prague); 2011; pp. 54-62; vol. 38, No. 2.

(Continued)

*Primary Examiner* — Ebony E Evans
(74) *Attorney, Agent, or Firm* — Kilpatrick Townsend & Stockton LLP

(57) ABSTRACT

Systems and methods for a mosquito fitness tester are disclosed. In one embodiment, a system includes: a rotatable enclosure comprising an enclosed cavity; a powertrain to rotate the rotatable enclosure in one or more axes; and one or more sensors to monitor one or more insects in the enclosed cavity.

12 Claims, 3 Drawing Sheets

(56) References Cited

U.S. PATENT DOCUMENTS

| | | | |
|---|---|---|---|
| 8,014,538 B2* | 9/2011 | Onishi | G10K 11/178 |
| | | | 381/71.14 |
| 8,705,017 B2 | 4/2014 | Hyde et al. | |
| 9,335,413 B2* | 5/2016 | Weber-Grabau | G01S 17/026 |
| 10,178,857 B2* | 1/2019 | Massaro | A01M 1/026 |
| 2008/0196672 A1* | 8/2008 | Mokhtarian | A01K 29/005 |
| | | | 119/421 |
| 2011/0132278 A1* | 6/2011 | Robinson, Jr. | A01K 67/033 |
| | | | 119/843 |
| 2013/0340319 A1* | 12/2013 | AlAyedh | A01M 1/106 |
| | | | 43/107 |

OTHER PUBLICATIONS

Ng'Habi, Kija R. et al.; "Effect of larval crowding on mating competitiveness of *Anopheles gambiae* mosquitoes"; BioMed Central; Malaria Journal; Sep. 30, 2005; pp. 1-9; vol. 4, No. 49; available via internet—http:/www.malariajournal.com/content/4/1/49.

* cited by examiner

SYSTEMS AND METHODS FOR A MOSQUITO FITNESS TESTER

BACKGROUND

All continents except Antarctica suffer from the plague of mosquito-vectored diseases. Various techniques for the control of mosquito populations involve the generation of sterile male insects for release into the wild for mating with local females. As a part of this development, it is important to assess the relative fitness of these male mosquitoes and their ability to compete with the local wild male population.

SUMMARY

In one embodiment, a system of the present disclosure may comprise: a rotatable enclosure comprising an enclosed cavity; a powertrain to rotate the rotatable enclosure in one or more axes; and one or more sensors to monitor one or more insects in the enclosed cavity.

Another embodiment of the present disclosure may comprise: an enclosed space comprising one or more insects; a processor to transmit output signals comprising data associated with insects; a plurality of output devices that receive the output signals and provide output; and one or more sensors to monitor the one or more insects and transmit sensor signals to the processor.

Another embodiment of the present disclosure may comprise a method comprising: stimulating an enclosure comprising one or more mosquitos; receiving a sensor signal comprising data associated with whether the one or more mosquitos are flying; determining information regarding the one or more mosquitos from the sensor signal; and determining a change to the stimulus to the enclosure based in part on the information.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

A full and enabling disclosure is set forth more particularly in the remainder of the specification. The specification makes reference to the following appended figures.

DETAILED DESCRIPTION

Figure 1:
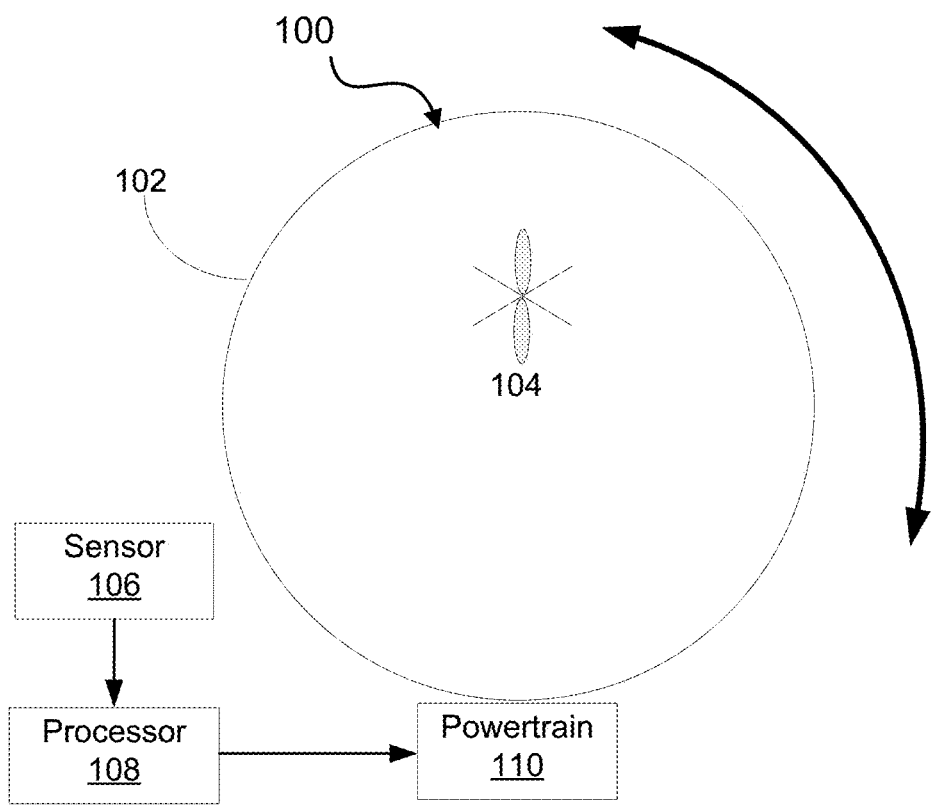
FIG. 1 shows an illustrative system for a mosquito fitness tester according to one embodiment of the present disclosure.

Reference will now be made in detail to various and alternative illustrative embodiments and to the accompanying drawings. Each example is provided by way of explanation, and not as a limitation. It will be apparent to those skilled in the art that modifications and variations can be made. For instance, features illustrated or described as part of one embodiment may be used in another embodiment to yield a still further embodiment. Thus, it is intended that this disclosure include modifications and variations as come within the scope of the appended claims and their equivalents.

Illustrative Example of a Mosquito Fitness Tester

A commercial rearing program may raise modified mosquitos for use in controlling a local mosquito population. For example, the rearing program may engineer mosquitos with desirable traits. These desirable traits may include sterility (or otherwise lacking the ability to produce viable offspring) and capable of competing with wild-type insects of the same species. In some embodiments, the reared insects may be male insects, e.g., sterile male mosquitos that are able compete with wild mosquitos in the area for mating partners. Other desirable traits may include, for example, longevity, size, flight capability, and/or heat-resistance. Prior to releasing the engineered mosquitos, researchers may wish to determine how well these mosquitos will compete with the local mosquito population for breeding partners. Researchers also desire to monitor the relative fitness of presently produced mosquitoes against those of prior batches in order to maintain a metric of quality control.

One illustrative embodiment of the present disclosure comprises a device for testing the fitness of an insect, e.g., a mosquito. The results of the fitness test may serve as a proxy for how effectively the mosquito will compete with the local population for mating partners. In one embodiment, a mosquito fitness tester may comprise an enclosure comprising one or more mosquitos. In such an embodiment the enclosure may comprise a substantially spherical or tubular shape. The mosquito fitness tester further comprises a powertrain to rotate the enclosure, e.g., an electric motor and a drive wheel. The rotation of the enclosure triggers the one or more mosquitos to loft, e.g., the mosquito will fly rather than turn upside down on an interior surface of the enclosure. In some embodiments, the interior surface may be designed to increase the difficulty of mosquitoes gaining purchase or may comprise a coating that increases the difficulty of the mosquitos gaining purchase. Thus, the mosquitos are motivated to fly when the surface is inclined or inverted. The illustrative mosquito fitness tester further comprises a sensor configured to monitor whether the mosquito is flying or landed. The sensor may be coupled to a processor, which based on data received from the sensor, modifies the operation of the powertrain to change the rotation of the enclosure.

An embodiment as described above may continue rotating the enclosure in one or more axes in a regular or random velocity, acceleration, or direction until the sensor determines that the mosquito will no longer fly. Alternatively, an embodiment may rotate for a predetermined period of time, stop rotating, and then begin rotating again once one or more of the mosquitos has landed on an interior surface of the enclosure. A further embodiment may rotate each time the mosquito lands and stop rotating when the mosquito is flying. These embodiments enable a researcher to determine the overall stamina of the mosquito, which the researcher may use as a proxy for the mosquito's ability to mate in the wild.

Another illustrative embodiment of the present disclosure comprises a device for testing the fitness of an insect, e.g., a mosquito. Such an embodiment comprises an enclosure comprising one or more mosquitos, a plurality of output devices, and one or more sensors to monitor the mosquitos. In one such embodiment, the enclosure may comprise a tube with an output device at either end of the tube. In such an embodiment, the tube may comprise a male mosquito. A processor may control the output devices to provide output associated with female mosquitos. For example, the output devices may comprise one or more of sound sources (e.g., speakers), light sources, vibrators, wind generators, and/or smell generators. The output may trigger the mosquito to fly toward (or away from) one of the output devices. A sensor, such as a light curtain at the middle of the tube may determine when the mosquito has crossed to one side of the tube. The sensor may transmit a signal associated with this movement to the processor, which then alternates which output device is activated.

Thus, in one such embodiment, the right output device may provide output associated with a female mosquito. When the sensor detects that the male mosquito moved to the right side of the tube, the processor may turn off the right output device and instead activate the left output device. This may trigger to the male mosquito to move back toward the left side of the tube. Such an embodiment enables the processor to determine the total time the mosquito continues to fly, as well as the mosquito's ability to track and locate female mosquitoes. This information may be used to determine the overall fitness of a type of mosquito, which may be used as a proxy for that mosquito's likely breeding success in the wild.

Another illustrative embodiment of the present disclosure comprises a device of the preceding design that utilizes as the output device, speakers playing sounds associated with an insect of the opposite sex. In such an embodiment, the sensor may include functionality to monitor the wing beat frequency of the insect under test ("IUT") and to modify the tone characteristics of the audio that is broadcast via the speakers. For example, male mosquitoes may adjust their frequency of wing beating to match harmonics with that of the pursued females. Thus one embodiment of the fitness tester comprises functionality to measure the male mosquito's ability to communicate with a female by using this frequency harmonic matching technique. Such an embodiment measures the characteristics of male mosquito's wing frequency as sounds associated with female wing beats are varied.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

Illustrative Systems for a Mosquito Fitness Tester

FIG. 1 shows an illustrative system 100 for a mosquito fitness tester according to one embodiment. As shown in FIG. 1, system 100 comprises an enclosure 102 comprising a mosquito 104. The system 100 further comprises a sensor 106, a processor 108, and a powertrain 110.

As shown in FIG. 1, the enclosure 102 comprises a substantially spherical enclosure 102. In other embodiments the enclosure may comprise any other suitable shape. For example, in some embodiments, enclosure 102 may comprise a tubular shape or a polygonal shape. In some embodiments, the enclosure 102 may comprise a clear material, e.g., glass or plastic. Alternatively, in some embodiments, the enclosure 102 may comprise an opaque material.

The enclosure 102 defines a cavity. One or more mosquitos 104 or other insects may be inserted into the cavity via an opening, such as a door or port. The one or more mosquitos 104 may comprise one or more species of mosquitos. In some embodiments, the interior walls of the enclosed cavity may comprise a modified surface, e.g., a polished surface for smoothness, a roughened surface, or a lubricated surface.

The system 100 further comprises a powertrain 110 configured to rotate the enclosure 102. In some embodiments, the powertrain 110 may comprise one or more electric motors (e.g., AC or DC motors) coupled to the enclosure 102. For example, the powertrain 110 may comprise an electric motor coupled to the enclosure 102 via a friction drive, e.g., in one embodiment the electric motor may drive a wheel that applies a rotary force to the enclosure 102. In some embodiments the powertrain 110 may rotate the enclosure 102 in a pattern (e.g., in one direction for a set time, then in another direction for a set time). In other embodiments, the powertrain 110 may rotate the enclosure 102 randomly, e.g., in multiple directions.

The system 100 further comprises a sensor 106 configured to monitor the mosquito 104. In some embodiments, the sensor 106 may comprise one or more of a camera, a microphone, a sensor that uses ultrasonic Doppler monitoring of wing movement, or a sensor that detects reflected optical signals. For example, the sensor may comprise a camera that tracks the location of mosquito 104 within the enclosure 102. In some embodiments, the sensor 106 is associated with a location in the enclosure 102, e.g., the sensor may comprise a pad at one end of the enclosure 102. In such an embodiment, the sensor 102 may determine when the mosquito 104 is roosting on the pad. Sensor 106 may be connected to Processor 108 directly, or wirelessly to allow for unrestricted movement of container 102. Sensor 106 may further comprise an independent power supply.

System 100 further comprises a processor 108. Processor 108 may comprise one or more of a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices. Further, the processor 108 may comprise or be in communication with memory, e.g., ROM, RAM, ASIC a floppy disk, CD-ROM, magnetic disk, memory chip, configured processor, all optical media, all magnetic tape or other magnetic media comprising executable program code.

As shown in FIG. 1, the processor 108 is coupled to sensor 106 and powertrain 110. In some embodiments the processor 108 may be configured to determine information based on signals received from the sensor 106 (e.g., the number of mosquitos, how long a mosquito has flown, how long a mosquito has roosted, whether a mosquito is roosting). Based on this information the processor 108 may control the operation of powertrain 110. For example, the processor may reduce or increase the speed of rotation, stop the rotation, or change the direction of rotation. For example, in one embodiment, upon determining that a mosquito has roosted for longer than a pre-determined period of time the processor 108 may control powertrain 110 to stop the rotation of enclosure 102. Further in some embodiments, the processor 108 may determine that a mosquito is in flight and thus control powertrain 110 to continue rotating enclosure 102.

Figure 2:
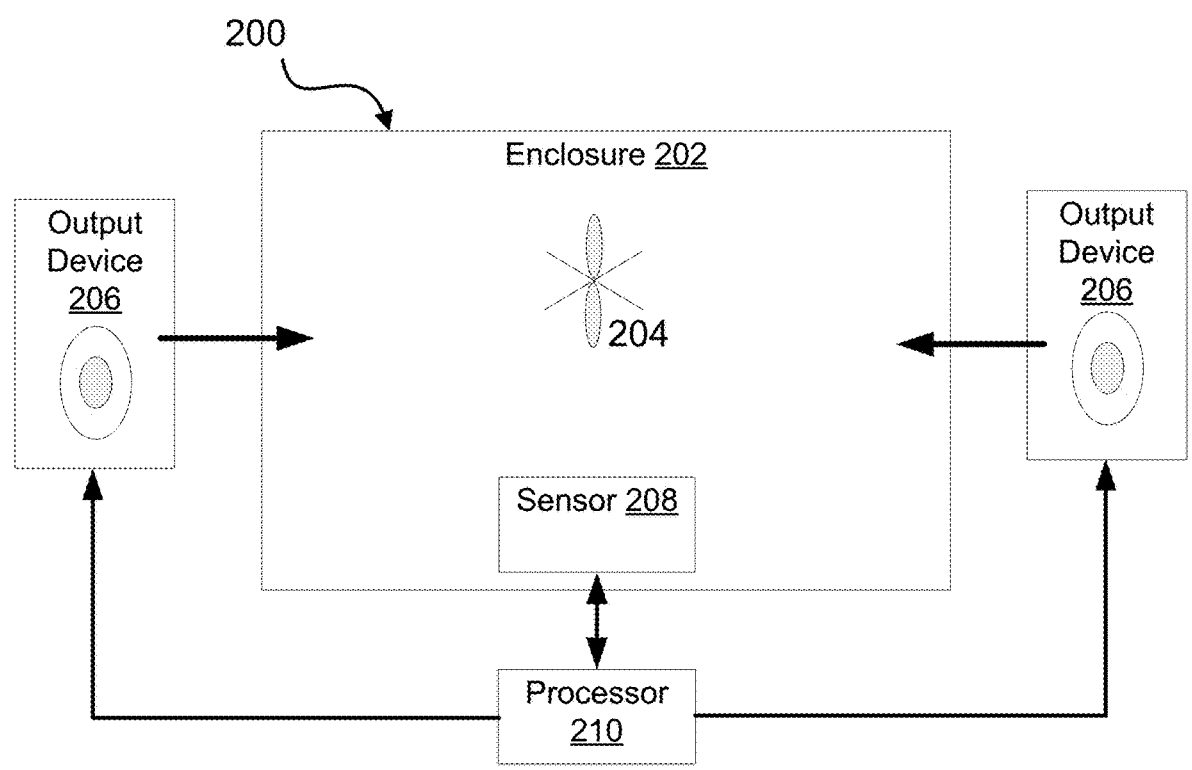
FIG. 2 shows another illustrative system for a mosquito fitness tester according to another embodiment of the present disclosure.

FIG. 2 shows another illustrative system 200 for a mosquito fitness tester according to another embodiment of the present disclosure. As shown in FIG. 2, the system 200 comprises an enclosure 202, a mosquito 204, two output devices 206, a sensor 208, and a processor 210.

As shown in FIG. 2, the enclosure 202 comprises a rectangular, box shaped, enclosure. However, any other shape enclosure may be used, e.g., a square shape or a tubular shaped enclosure. In some embodiments, the enclosure 202 may comprise a clear material, e.g., glass or plastic. Alternatively, in some embodiments, the enclosure 202 may comprise an opaque material. Enclosure 202 defines a cavity. One or more mosquitos 204, or other insects, may be inserted into the cavity, e.g., via a door or a port. The one or more mosquitos 204 may comprise one or more species of mosquitos.

The system further comprises a plurality of output devices 206. Output devices 206 comprise one or more devices configured to provide output to enclosure 202. For example, output devices 206 may comprise one or more of sound sources (e.g., speakers), light sources, vibrators, wind generators, and/or smell generators. For example, in one embodiment, output devices 206 comprise any speakers configured to output sounds or vibrations that are perceptible to insects, e.g., mosquitos. Output devices 206 are controlled by processor 210.

Processor 210 comprises a processor similar to processor 108 described above with regard to FIG. 1. Processor 210 is configured to control output devices 206 to provide output associated with insects, e.g., mosquitos. This output, e.g., vibrations, light, smells, or sounds may trigger the mosquito 204 to fly toward an output device providing the output. In some embodiments, the sounds may be associated with a mosquito of the opposite sex, e.g., if the mosquito 204 comprises a male mosquito, the sounds may be associated with a female mosquito. Further, in some embodiments, these sounds may be output at a frequency corresponding to the wing beat pattern of the mosquito, e.g., the sounds may be modulated based on harmonics of the wing beat pattern of mosquito 204.

The system 100 further comprises a sensor 208. In one embodiment, the sensor 208 may comprise a light curtain, e.g., a light curtain located at the middle of the enclosure 202. In other embodiments, the sensor 208 may comprise one or more of: a camera, a microphone, a sensor that uses ultrasonic Doppler monitoring of wing movement, or a sensor that detects reflected optical signals. The sensor 208 may detect when the mosquito 204 has crossed to one side of the enclosure 202. The sensor may transmit a signal associated with this movement to the processor 210, which then alternates which output device 206 is providing output. Thus, in one such embodiment, the right output device 206 may comprise a speaker playing sounds associated with a female mosquito. When the sensor 208 detects that the male mosquito 204 moved to the right side of the tube, the sensor 208 may transmit a signal to the processor, and in response to receiving the signal, the processor 210 may turn off the right speaker 206 and play sounds associated with a female mosquito from the left speaker 206. This may trigger the male mosquito 204 to move back toward the left side of the tube.

In other embodiments, rather than a single sensor 208, the system 200 may comprise a plurality of sensors, e.g., one at each end of enclosure 202. Some embodiments of the system described with regard to FIG. 2 enable the processor 210 to determine the total time the mosquito 204 continues to fly. This information may be used to determine the overall fitness of a type of mosquito 204, which may be used as a proxy for that mosquito's breeding in the wild.

Illustrative Methods for a Mosquito Fitness Tester

Figure 3:
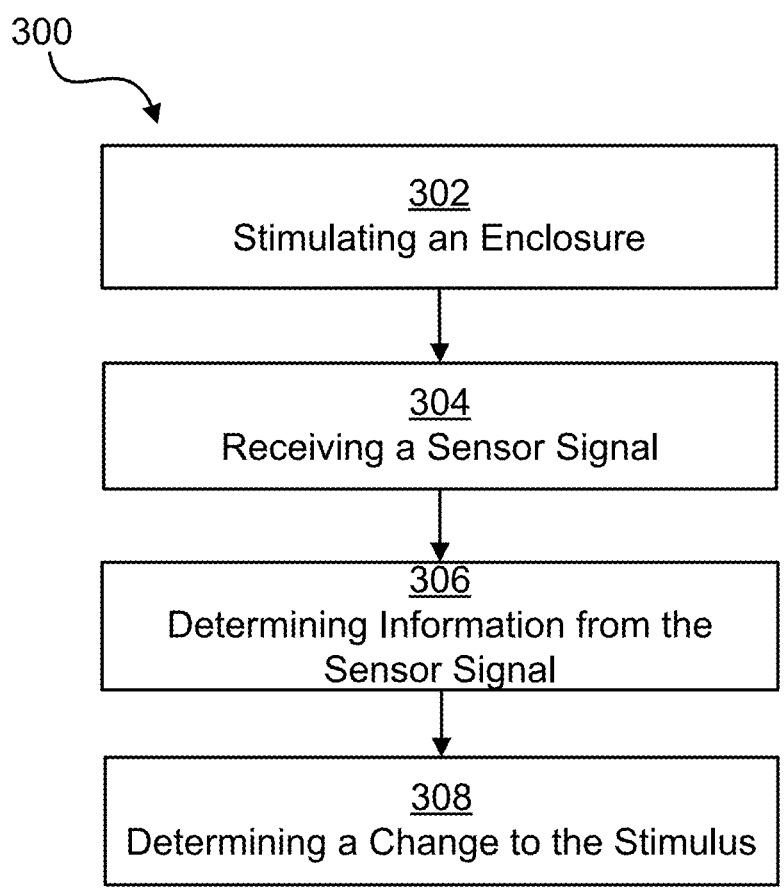
FIG. 3 is a flow chart for a method for testing mosquito fitness according to one embodiment of the present disclosure.

FIG. 3 is a flow chart for a method of operating a mosquito fitness tester according to one embodiment. In some embodiments, the steps in FIG. 3 may be implemented in program code executed by a processor. In some embodiments, these steps may be implemented by a group of processors. In some embodiments the steps shown in FIG. 3 may be performed in a different order. Alternatively, in some embodiments, one or more of the steps shown in FIG. 3 may be skipped, or additional steps not shown in FIG. 3 may be performed. The steps below are described with reference to components described above with regard to system 100 shown in FIG. 1 and/or the system 200 shown in FIG. 2.

The method 300 begins at step 302 when an enclosure 102 is stimulated. The enclosure 102 contains one or more mosquitos 104. As described above, the stimulus may comprise rotating the enclosure. Rotating the enclosure may cause the mosquito to loft, e.g., so the mosquito avoids being upside down on the interior of the enclosure 102. In other embodiments, the stimulus may comprise providing output from, e.g., one or more of sound sources (e.g., speakers), light sources, vibrators, wind generators, and/or smell generators. For example, the output devices 206 may comprise speakers, which may output sounds associated with a mosquito of the opposite sex from mosquito 104. Such sounds may be output by one or more of a plurality of speakers mounted proximate to or within a suitable enclosure.

At step 304 the processor 108 receives a sensor signal from sensor 106. The sensor signal may comprise information associated with the mosquito. For example, the sensor signal may indicate whether the mosquito has lofted or roosted. Further, in some embodiments, the sensor signal may indicate the location of mosquito 104 in the enclosure. For example, the sensor signal may indicate that the mosquito has moved to one side of the enclosure 102.

Then the processor 108 determines information from the sensor signal 306. In some embodiments this information may comprise the status or location of the mosquito 104. For example, the information may be whether the mosquito has lofted or roosted and for how long. Further, the information may comprise the location of mosquito 104 within the enclosure.

At step 308, the processor 108 determines a change to the stimulus. In some embodiments the change to the stimulus may comprise controlling powertrain 110 to speed, slow, or stop the rotation of enclosure 102. Further the change to the stimulus may comprise changing the direction of rotation of the enclosure 102. Alternatively, in some embodiments, changing the stimulus may comprise changing which output device 206 is providing output. For example, the processor 110 may control the output devices 206 to provide output from only the output device furthest from the mosquito 104. Alternatively, if the mosquito has roosted for a certain length of time, the processor 110 may control the output devices 206 to stop output.

Advantages of a Mosquito Fitness Tester

There are numerous advantages of a mosquito fitness tester. Embodiments of the present disclosure enable researchers to determine an insect, such as a mosquito's ability to fly over a period of time or its ability to detect and adapt to females in its vicinity. This information may enable researchers to determine how effectively a laboratory-reared insect will compete with other insects in breeding. This is an improvement over other methods of analyzing a mosquito, e.g., simply measuring the mosquito's size, because size may be a less accurate proxy for effective breeding than total flight time. Further, embodiments of the present disclosure may enable the characterization of a mosquito's breeding competitiveness, which may be important to determine the number of sterile mosquitoes which must be released to effectively suppress a wild population.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered. Accordingly, the above description does not bound the scope of the claims.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs including a sensor sampling routine, selection routines, and other routines to perform the methods described above.

Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example tangible computer-readable media, that may store instructions that, when executed by the processor, can cause the processor to perform the steps described herein as carried out, or assisted, by a processor. Embodiments of computer-readable media may comprise, but are not limited to, all electronic, optical, magnetic, or other storage devices capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. Also, various other devices may include computer-readable media, such as a router, private or public network, or other transmission device. The processor, and the processing, described may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

What is claimed:

1. A system comprising:
a rotatable enclosure comprising an enclosed cavity;
a powertrain to rotate the rotatable enclosure in one or more axes;

one or more sensors to monitor one or more insects in the enclosed cavity; and a processor coupled to the powertrain and the one or more sensors and configured to:

control the powertrain to rotate the enclosure in a first direction, wherein the powertrain is configured to rotate the enclosure in both the X axis and the Y axis;

detect that one or more insects have lofted based on data received from the one or more sensors; and control the powertrain to rotate the enclosure in a second direction based in part on whether the one or more insects have lofted.

2. The system of claim 1, wherein the rotatable enclosure comprises the shape of: a sphere or a tube.

3. The system of claim 1, wherein the one or more insects comprise mosquitos.

4. The system of claim 1, wherein the one or more sensors are sensors that monitor whether the one or more insects are flying.

5. The system of claim 1, wherein the one or more sensors comprise one or more of:

a camera, a microphone, an ultrasonic Doppler sensor, or a light sensor.

6. The system of claim 1, wherein the powertrain comprises one or more electric motors.

7. The system of claim 6, wherein the powertrain further comprises one or more wheels, and wherein the rotatable enclosure is positioned on the one or more wheels and configured to rotate based on rotation of the one or more wheels.

8. A method comprising:

stimulating an enclosure comprising one or more mosquitos;

receiving a sensor signal comprising data associated with whether the one or more mosquitos are flying;

determining information regarding the one or more mosquitos from the sensor signal; and determining a change to a stimulus to the enclosure based in part on the information, wherein the stimulus comprises rotating the enclosure in a substantially random direction in both the X and Y axis.

9. The method of claim 8, wherein changing the stimulus to the enclosure comprises one or more of: stopping the rotating, starting the rotation, changing a direction of rotation, or changing a speed of rotation.

10. The method of claim 8, wherein stimulating an enclosure further comprises outputting sounds associated with mosquitos.

11. The method of claim 10, wherein the change to the stimulus comprises changing a speaker that outputs the sounds.

12. The method of claim 10, wherein the sounds are sounds associated with mosquitos of a sex opposite that of the one or more mosquitos.

\* \* \* \* \*